United States Patent [19]
Rolt et al.

[11] Patent Number: 5,501,655
[45] Date of Patent: Mar. 26, 1996

[54] APPARATUS AND METHOD FOR ACOUSTIC HEAT GENERATION AND HYPERTHERMIA

[75] Inventors: Kenneth D. Rolt, Medford; Padmakar P. Lele, Westford, both of Mass.

[73] Assignee: Massachusetts Institute of Technology, Cambridge, Mass.

[21] Appl. No.: 275,809

[22] Filed: Jul. 15, 1994

Related U.S. Application Data

[63] Continuation of Ser. No. 861,187, Mar. 31, 1992, abandoned.

[51] Int. Cl.⁶ .................................................. A61N 7/02
[52] U.S. Cl. ..................... 601/3; 601/2; 128/660.03; 607/97; 607/154
[58] Field of Search ................ 601/2, 3; 128/660.03; 600/10; 607/96, 97, 154

[56] References Cited

U.S. PATENT DOCUMENTS

| | | |
|---|---|---|
| 3,763,463 | 10/1973 | Muir . |
| 4,343,301 | 8/1982 | Indech ............................. 128/24 AA |
| 4,441,486 | 4/1984 | Pounds ............................ 128/24 A |
| 4,586,512 | 5/1986 | Do-huu et al. ................... 128/660 |
| 4,622,972 | 11/1986 | Giebeler, Jr. .................... 128/399 |
| 4,646,756 | 3/1987 | Watmough et al. ............. 128/24 AA |
| 4,798,215 | 1/1989 | Turner ............................. 128/804 |
| 4,815,479 | 3/1989 | Carr ................................. 128/804 |
| 4,836,191 | 6/1989 | Noske et al. .................... 128/24 A |
| 4,860,752 | 8/1989 | Turner ............................. 128/804 |
| 4,875,487 | 10/1989 | Seppi ............................... 128/660.03 |
| 4,889,122 | 12/1989 | Watmough et al. ............. 128/399 |
| 4,893,624 | 1/1990 | Lele .................................. 128/399 |
| 4,936,303 | 6/1990 | Detwiler et al. ................. 128/24 AA |
| 4,938,216 | 7/1990 | Lele .................................. 128/399 |
| 4,938,217 | 7/1990 | Lele .................................. 128/399 |
| 4,957,099 | 9/1990 | Hassler ............................. 128/660.03 X |
| 4,960,109 | 10/1990 | Lele .................................. 128/736 |
| 5,123,404 | 6/1992 | Takayama ......................... 601/4 |
| 5,209,234 | 5/1993 | LaRocca ........................... 128/660.03 |
| 5,230,334 | 7/1993 | Klopotek ........................... 128/24 AA |

FOREIGN PATENT DOCUMENTS

| | | |
|---|---|---|
| 0332871 | 9/1989 | European Pat. Off. . |
| 3709404 | 11/1988 | Germany . |
| 2126901 | 4/1984 | United Kingdom . |

OTHER PUBLICATIONS

"Temperature Elevation in Tissues Generated by Finite-amplitude Tone Bursts of Ultrasound" by Wu and Du, J. Acoust. Soc. Am, 88(3), Sep. 1990, pp. 1562–1577.
Carpenedo, et al. (1987) Acoustics Letters, vol. 10, No. 11, pp. 178–181.
Dunn, et al. (1965) J. Sound Vib. vol. 2, No. 4, pp. 471–476.
Lele, et al. (1982) Br. J. Cancer, vol. 45, Suppl. V, 108, pp. 109–121.
Fessenden, et al. (1984) IEE, vol. BME–31, No. 1 pp. 126–135.
Nishimura, et al. (1984) Jap. J. of Appl. Phys. vol. 23, Suppl. 23–1, pp. 221–223.

Primary Examiner—William E. Kamm
Assistant Examiner—Brian L. Casler
Attorney, Agent, or Firm—Palmer & Dodge

[57] ABSTRACT

An ultrasound hyperthermia applicator suitable for medical hyperthermia treatment, and method for using the same, includes two ultrasound sources producing focused ultrasound beams of frequencies $f_0$ and $f_1$. An aiming device directs the two ultrasound beams so that they cross each other confocally at the target. A controller activates the two ultrasound sources so that the target is simultaneously irradiated by the two focused ultrasound beams. The two ultrasound sources provide acoustic energy sufficient to cause significant intermodulation products to be produced at the target due to the interaction of the two ultrasound beams. The intermodulation products are absorbed by the target to enhance heating of the target. In preferred embodiments the ultrasound sources include pair of signal generator for producing gated ultrasound output signals driving single crystal ultrasound transducers. In other embodiments the ultrasound sources include a pair of phased array ultrasound transducers for generating two steerable ultrasound beams. An aiming device is provided for electronically steering and focusing the two ultrasound beams so that they cross each other confocally at the target. Further embodiments employ pluralities of transducers, arrays, or both.

44 Claims, 7 Drawing Sheets

ARRANGEMENT FOR TEMPERATURE
MEASUREMENT OF INTERSECTING FOCUSED
ULTRASOUND TRANSDUCERS

REFRACTION OF OBLIQUE FOCUSED WAVES

APPARATUS AND METHOD FOR ACOUSTIC HEAT GENERATION AND HYPERTHERMIA

This is a continuation of application Ser. No. 07/861,187 filed on Mar. 31, 1992 now abandoned

BACKGROUND OF THE INVENTION

This invention relates to a method for generating localized heat within materials and biological tissue by the means of intersecting beams of ultrasound.

High frequency acoustic waves, or ultrasound, may be used to remotely heat industrial or biological materials. There has been strong evidence in research and clinical laboratories that focused ultrasound for cancer hyperthermia will become a useful mode of treating cancer patients, in addition to the surgical, radiological and chemotherapeutic methods that are available now. In the treatment of tumors in cancer hyperthermia, focused ultrasound heats the tumor to a temperature of approximately 43° C. while the adjacent healthy tissue is kept at a lower temperature closer to normal body temperature (37° C.). The elevated temperature in the tumor disrupts the tumor growth and eventually kills it. This allows the cancer to potentially be treated without surgery, without ionizing radiation, or without chemotherapy.

Conventional focused ultrasound for heating is employed by using either a scanned ultrasound transducer or with a phased array. The scanned transducer uses a lens, much like an optical magnifying glass focuses sunlight, while the phased array uses electronic delays among the array elements to achieve focusing. A burst of sound is then emitted which converges at the focus to provide localized high intensity acoustic energy. Some of the high intensity acoustic energy is absorbed by the tissue at the focus and is dissipated as concentrated focal heat. The rest of the energy travels through the focus and is slowly dissipated into the surrounding tissues as distributed heat.

Biomedical hyperthermia applicators using a plurality of sound sources to heat larger, distributed volumes, have also been investigated. These investigations have relied upon linear thermal superposition of the plurality of sound sources to heat the target tissues. Nonlinear effects of sound propagation through animal tissue and materials have also been studied for a single sound source.

The nonlinear mixing, or intermodulation, of sound waves has been known in oceanographic acoustics. Oceanographic acoustic applications have used both the linear (superposition) and nonlinear (intermodulation) effects of intersecting sound beams. Nonlinear acoustic sonars, known as oceanographic parametric sonars, deliberately promote the generation of a difference frequency to enhance sonar beamforming and long range sound propagation. The generated difference frequency is usually 30 to 60 dB below the level of the primary frequencies. A second product of nonlinear mixing is the sum frequency, which is generated by the intermodulation process at 10 to 40 dB below the level of the primary frequencies, indicating that the conversion from primary to sum frequency is a significantly more efficient process than the conversion of a primary to a difference frequency. Since higher frequencies are subject to higher absorption coefficients in water they generate more heat than the primary frequencies as they propagate, but propagate shorter distances than the primary frequencies. In oceanographic sonar applications, heat generation via sound absorption is generally an undesirable result of nonlinear intermodulation.

SUMMARY OF THE INVENTION

Little or no use has been made of the sum frequency in hyperthermia applications. However, the sum frequency component of nonlinear mixing, as well as the harmonics created by high intensity sound waves, are useful for enhanced heating of localized areas. The present invention provides a hyperthermia apparatus and method which exploits the nonlinear propagation properties of sound, and the nonlinear mixing of sound, to enhance heating of the target. The invention is particularly useful for hyperthermia treatment of deep seated biological tissues. The invention is also suited for heating in materials processing.

In one aspect of the invention an ultrasound hyperthermia applicator, and method for using the same, includes at least two ultrasound sources producing focused ultrasound beams of frequencies $f_0$ and $f_1$. The two ultrasound beams are aimed so that they cross each other and are focused at the same spot on the target, i.e., they are confocused at the target. A controller activates the two ultrasound sources so that the target is simultaneously irradiated by the two focused ultrasound beams. The two ultrasound sources provide acoustic energy sufficient to cause significant intermodulation products to be produced at the target due to the interaction of the two ultrasound beams. The intermodulation products are absorbed by the target to enhance heating of the target.

In preferred embodiments frequency $f_0$ is substantially the same as frequency $f_1$. The target is a tissue mass located within the human body, and frequencies $f_0$ and $f_1$ are chosen for useful penetration to the target tissue. Preferably, the target is a tissue mass located within the cranium.

In other preferred embodiments the ultrasound sources include signal generators for producing gated ultrasound output signals at frequencies $f_0$ and $f_1$ in response to an input control signal generated by a controller. A power amplifier is coupled to the output of each signal generator, and an ultrasound transducer is coupled to the output of each power amplifier to convert each amplified ultrasound signal into a focused ultrasound beam. Each ultrasound transducer includes an acoustic lens for focusing its corresponding ultrasound beam at the target. Aiming means are provided for fixing the ultrasound transducers relative to each other so that the ultrasound beams cross each other at a predetermined angle.

In yet another preferred embodiment frequency $f_0$ is substantially the same as frequency $f_1$ and the ultrasound sources include a signal generator for producing a gated ultrasound signal at frequency $f_0$ in response to an input control signal generated by a controller. A power amplifier is coupled to the output of the signal generator, and a power splitter is coupled to the output of the amplifier for dividing the amplified gated ultrasound signal between two ultrasound transducers.

In still another preferred embodiment the ultrasound sources include at least a pair of phased array ultrasound transducers coupled to corresponding ultrasound scanners for generating two steerable ultrasound beams. Aiming means are provided for electronically steering and focusing the two ultrasound beams so that they cross each other confocally at the target.

In still another preferred embodiment, a plurality of focused ultrasound sources, directed in a confocal manner, are each driven by a continuous wave (CW) signal, or a pulsed wave (PW) signal, or a modulated signal, which is centered about $f_0$, $f_1$ or $f_n$ for an n-source configuration. Center frequencies $f_0, f_1, \ldots, f_n$ can be substantially the same. The modulation can be in the form of amplitude modulation (AM), frequency modulation (FM) such as in an FM-sweep, or 'chirp', or in the form of a pseudo-random modulation.

Thus, the invention described herein achieves efficient delivery and conversion of acoustic energy to enhance heating of a hyperthermia target by producing intermodulation products at the target, or confocal region, which are easily absorbed by the target to produce heat. This invention improves upon focused ultrasound hyperthermia techniques by deliberately exploiting the nonlinear propagation of sound at high intensities to enhance heating. The nonlinear interaction, which generates additional heat, does so only within the confines of the confocal region. The invention can advantageously be used to efficiently heat deep seated biological tissue targets without excessively heating surrounding tissues since the acoustic energy is delivered to the target in the form of relatively low frequency acoustic energy, which is not easily absorbed by the surrounding tissues. Further, the invention delivers the acoustic energy to the target in a plurality of crossed ultrasound beams focused at the target which advantageously minimizes the acoustic intensity in the surrounding tissues, and maximizes the acoustic intensity at the target.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DESCRIPTION OF THE PREFERRED EMBODIMENT

Figure 1:
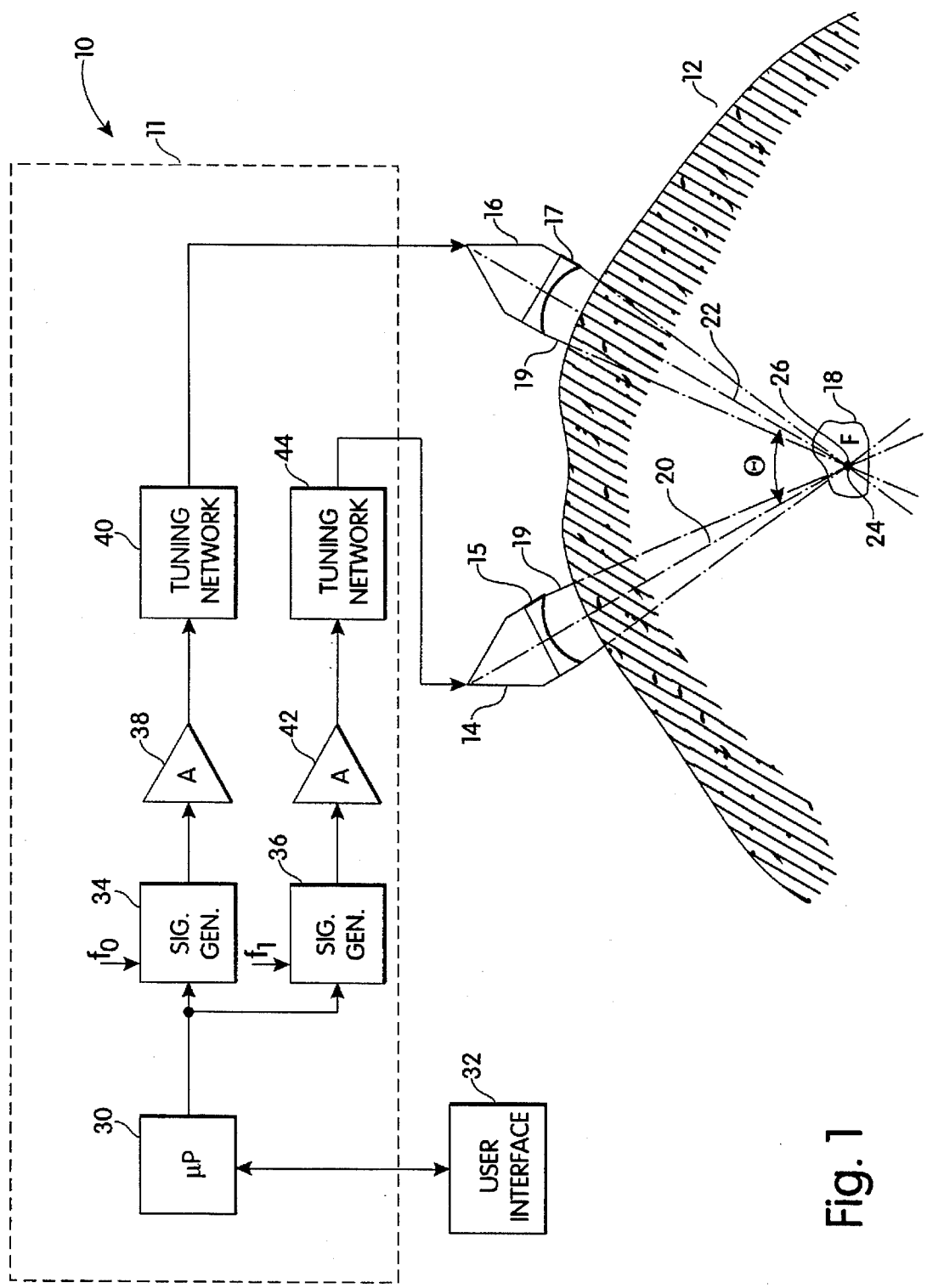
FIG. 1 is schematic block diagram of the ultrasound hyperthermia applicator of this invention which features two ultrasound transducers producing interacting focused ultrasound beams at independent operating frequencies.

Referring to FIG. 1, a preferred embodiment of a hyperthermia applicator 10 for heating biological tissue includes a hyperthermia controller 11 and two ultrasonic transducers 14 and 16 for emitting ultrasound energy which is acoustically coupled to a target body 12 to heat a localized region of tissue 18 deep within the target body. Transducer 14 and transducer 16 each produce a focused beam of acoustic energy 20 and 22, respectively, at or near the same frequency. The ultrasound frequency range typically employed for heating biological tissue is from about 50 kHz to over 5 MHz. Transducers 14 and 16 have focusing lenses, 15 and 17 respectively, which in turn are coupled to the target body by coupling means 19 known in the art. The transducers are oriented against the body 12 so that the focused beams 20 and 22 cross each other at their respective foci 24, 26 and within the localized volume of tissue 18 which represents a system confocal region F.

The intersection and consequent nonlinear interaction of intersecting waves promotes the generation of sum-frequencies by intermodulation especially in the interaction (confocal) region, and this in turn accentuates the generation of heat. Focused intersecting beams having coincident foci increase the acoustic intensity at the confocal region over otherwise unfocused intersecting beams. Higher intensities at the confocal region promote nonlinear acoustic effects and lead to greater temperature rise. Outside the confocal region where the acoustic intensity is significantly less, nonlinear effects are reduced and hence less heat is deposited. By limiting the intersection, and hence interaction, of two or more sound beams to a certain volume, heat generation due to nonlinear interaction is accentuated within the region, and minimized outside the region. More energy deposition in a confocal region by nonlinear interaction means more heat in the confocal region and less acoustic energy which continues past the confocal region to be absorbed in healthy tissue elsewhere.

Hyperthermia controller 11 includes a microprocessor 30 which communicates with a user interface 32, such as a keyboard and display, and generates timing and control signals to simultaneously activate a pair of ultrasound signal generators 34 and 36. Signal generator 34 produces a pulsed ultrasound signal at a frequency $f_0$, gated on and off by the microprocessor 30, which is amplified by amplifier 38. The output of amplifier 38 drives ultrasound transducer 16 through an impedance matching, or tuning network, 40. Similarly, signal generator 36 produces a pulsed ultrasound signal at a frequency $f_1$, gated on and off by the microprocessor 30, which is amplified by amplifier 42. The output of amplifier 42 drives ultrasound transducer 14 through an impedance matching, or tuning network, 44. Ultrasound frequencies $f_0$ and $f_1$ are typically the same, or near each other.

Figure 2:
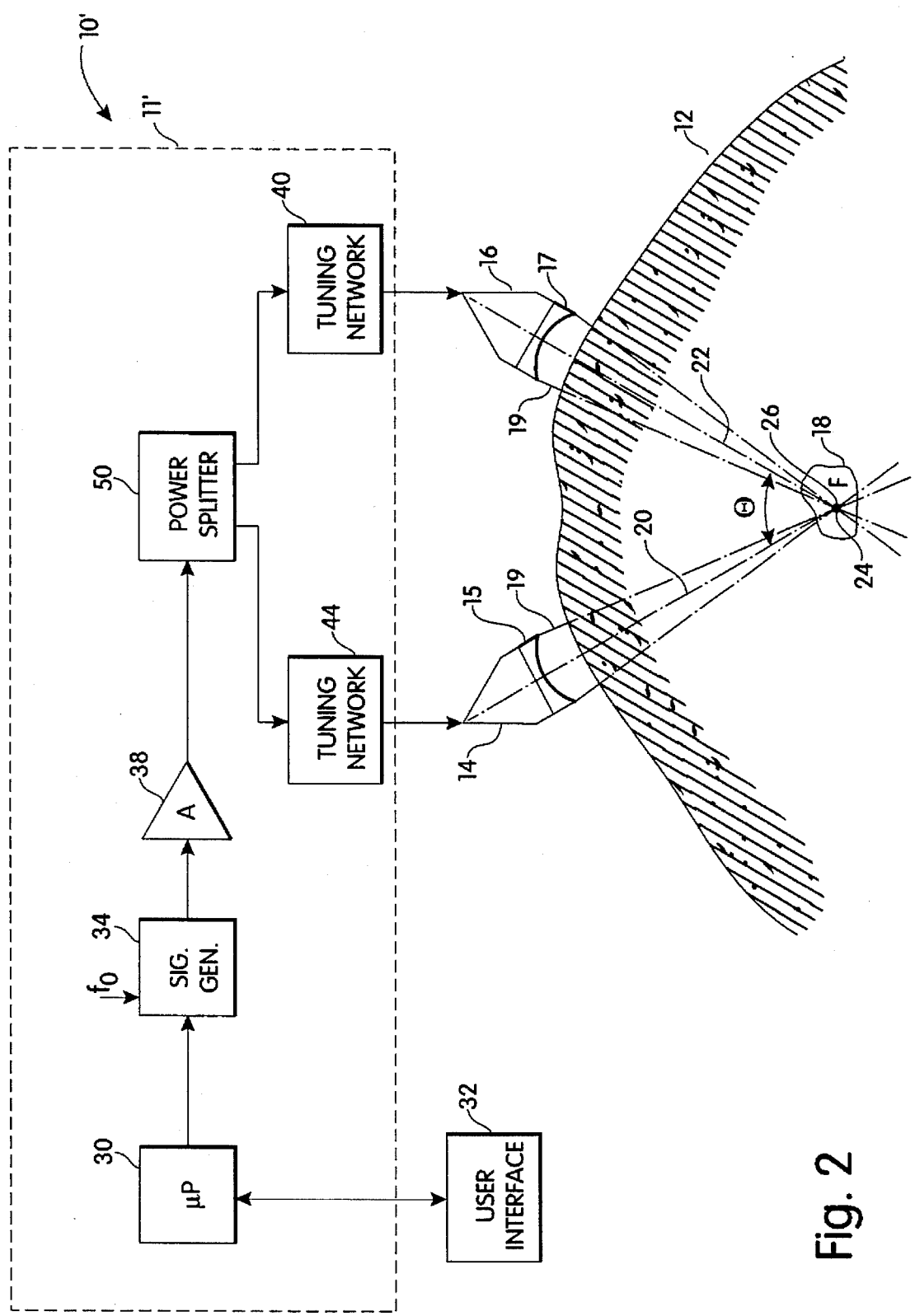
FIG. 2 is a schematic block diagram of another ultrasound hyperthermia applicator of this invention which features two ultrasound transducers producing interacting focused ultrasound beams at the same operating frequency.

Referring to FIG. 2, an alternative preferred embodiment of a hyperthermia applicator 10' includes a hyperthermia controller 11' having a power splitter 50 for driving the ultrasound transducers 14 and 16 at the same ultrasound frequency. In this embodiment, signal generator 34 produces a pulsed ultrasound signal at frequency $f_0$, gated on and off by microprocessor 30, which is amplified by amplifier 38 to drive the input to the power splitter 50. Power splitter 50 divides the power of the amplified ultrasound signal and applies it equally to each transducer 14 and 16 through its respective tuning network 44 and 40.

Each transducer 14 and 16 (FIG. 1 or FIG. 2) includes an acoustic lens portion 15 and 17, respectively, for focusing the resulting ultrasound beam deep within the target 12. The lens portion of each ultrasound transducer is acoustically coupled to the target body 12 by providing fluid or acoustic gel (not shown) in the gap 19 which forms between each transducer and the target body. Alternatively, the entire target body/transducer interface may be immersed in fluid to aid acoustic coupling.

Transducer 14 is arranged so that the main acoustic beam 20 generated by the transducer has its focus 24 located at the desired focal region F of tissue target 18. Similarly, transducer 16 is arranged to have the focus 26 of its main acoustic beam 22 coincident with focus 24 of acoustic beam 20. The transducers 14 and 16 are further arranged so that the center of acoustic beam 20 is offset from the center of acoustic beam 22 by an angle θ. Angle θ is typically any angle other than 0° and 180°.

Figure 3:
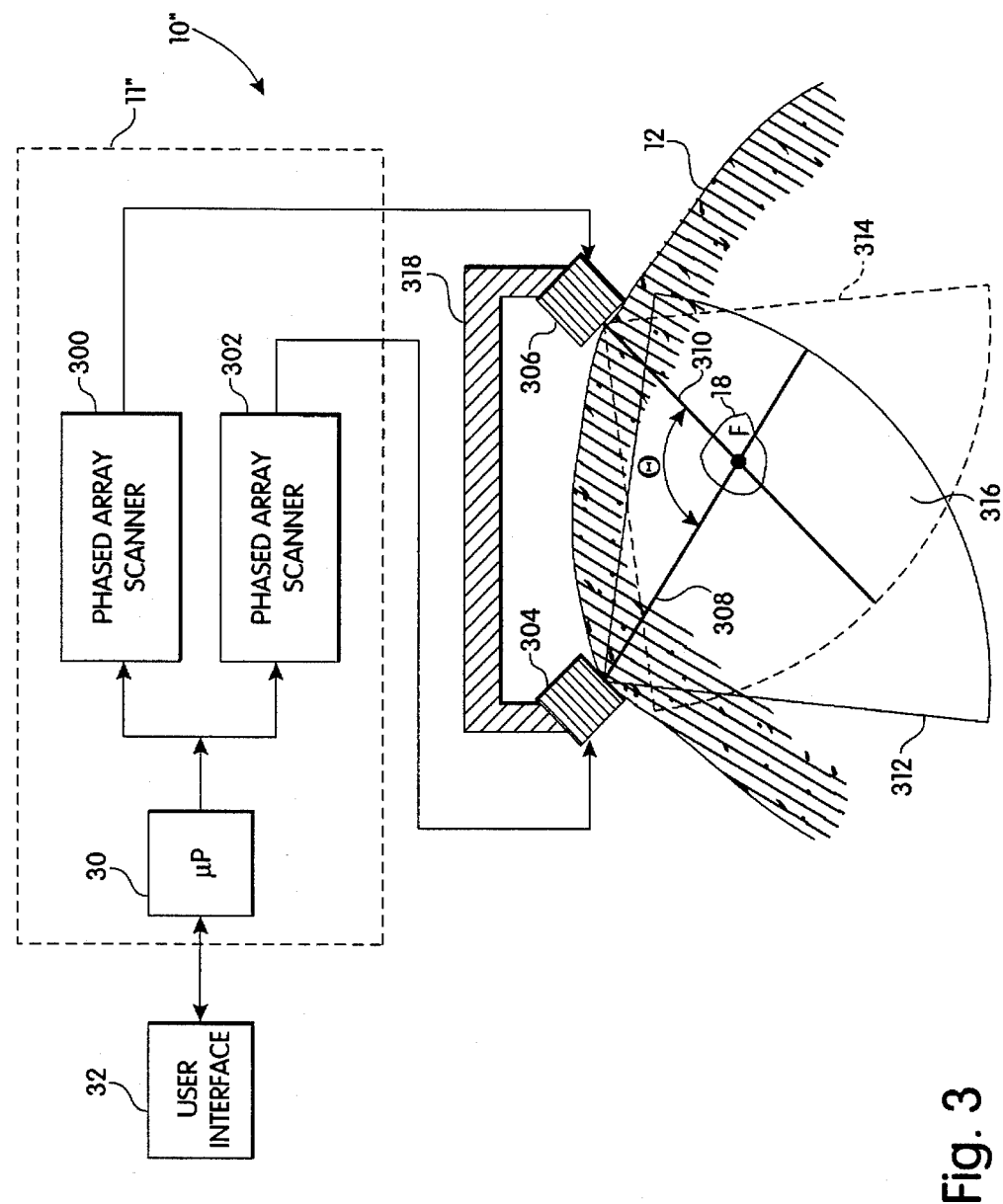
FIG. 3 is a schematic block diagram of another ultrasound hyperthermia applicator of this invention which features two phased array ultrasound transducers having electronically steered and focused interacting ultrasound beams.

Referring to FIG. 3, another alternative preferred embodiment of a hyperthermia applicator 10" includes a hyperthermia controller 11" having two phased array scanners 300 and 302 for driving respective phased array ultrasound transducers 304 and 306. Each ultrasound phased array transducer 304 and 306 includes a plurality of individually driven transducer elements for producing an electronically steered and focused ultrasound beam 308 and 310, respectively. The ultrasound signals required to steer and focus the ultrasound beams are produced by each of the corresponding phased array scanners in a manner well understood by those skilled in the art. Microprocessor 30 coordinates the operation of the two phased array scanners 300 and 302 to form beams 308 and 310.

Each phased array transducer 304 and 306 is capable of forming a focused beam within its respective sector 312 and 314. Thus, the two beams 308 and 310 can be electronically steered to cross each other anywhere within the three-dimensional overlap 316 of sectors 312 and 314. Each beam can be electronically focused at the selected beam crossing site F. The two phased array transducers can be fixed relative to each other by attachment to a rigid structure 318. The beams generated by each transducer are electronically aimed and focused to cross each other at a plurality of confocal points located in 316, as a function of time. This preferred embodiment thus allows for a wide range of electronically selectable treatment sites within the target body 12.

This invention is particularly well-suited for heating biological tissue in vivo for therapeutic purposes without invasive surgery, for hyperthermia treatment of cancerous tumors, and for ablation of target volumes of tissues. The utilization of this invention will be important in many areas, such as transmission of ultrasound at relatively low ultrasound frequencies through different portions of the skull but coincident within a treatment volume in the brain, and in treatment of tissues overlying a critical tissue such as bone or lung which must be spared from heating.

The heat generation results from the transformation of acoustic waves into heat. Heat generation depends on the acoustic absorption coefficient of the medium, the acoustic intensity, and the frequency of the acoustic waves. Acoustic absorption and heating increases as the frequency and intensity of the acoustic waves increases. This invention recognizes that simultaneous bursts of sound from separate sources converging upon the same focal location will effect a linear adding of heat at the focus, as well as interact with each other in a nonlinear manner to produce mixed-frequency energy at the focus which provides extra heating at the focus. This extra heating means more heating at the confocal region F, where it is desired, and less heating elsewhere, where it is undesired.

This invention is particularly useful in heating cranial targets without surgery because the primary transmit frequencies may be made low enough to penetrate the skull with low absorption and low scattering. Thus, sufficient acoustic energy would survive the passage through the skull so that nonlinear interaction of intersecting beams at the target would give rise to useful localized heat generation.

This invention is not limited to only two transducers, or two transducer arrays, since the nonlinear heating effect at the tissue target 18 is caused by the confocal intersection of two or more beams. It will be apparent to those skilled in the art that almost any plurality of transducer sources, and associated driving circuitry, can be used to effect similar nonlinear results. The plurality of transducer sources can emit pulses which are similar in frequency content or pulses which are substantially different in frequency content. The frequency content of the pulses can include pure CW tones, or modulated bandlimited frequencies. The acoustic drive characteristics of the transducers can also be used to determine the frequency content of the pulses. For instance, overdriving a transducer often produces triangular wave output signals which are rich in harmonics of the fundamental driving frequency. It should be noted that the intermodulation of broadband signals which are rich in harmonics produce a similarly rich variety of mixing products at frequencies which are easily absorbed by the target to produce excess heat.

Furthermore, while focusing the beams at the target site increases the acoustic intensity to enhance intermodulation at the site, unfocused beams may also be used if they can deliver sufficient acoustic intensity at the site to provide similar intermodulation results. However, acoustic power levels must remain below that which will cause excess heating to the surrounding tissues or cavitation of the tissue medium. Therefore, focused ultrasound beams are a more practicable means for delivering high intensity acoustic power to a deep seated target site than unfocused ultrasound beams.

Eperimental Results

Figure 4:
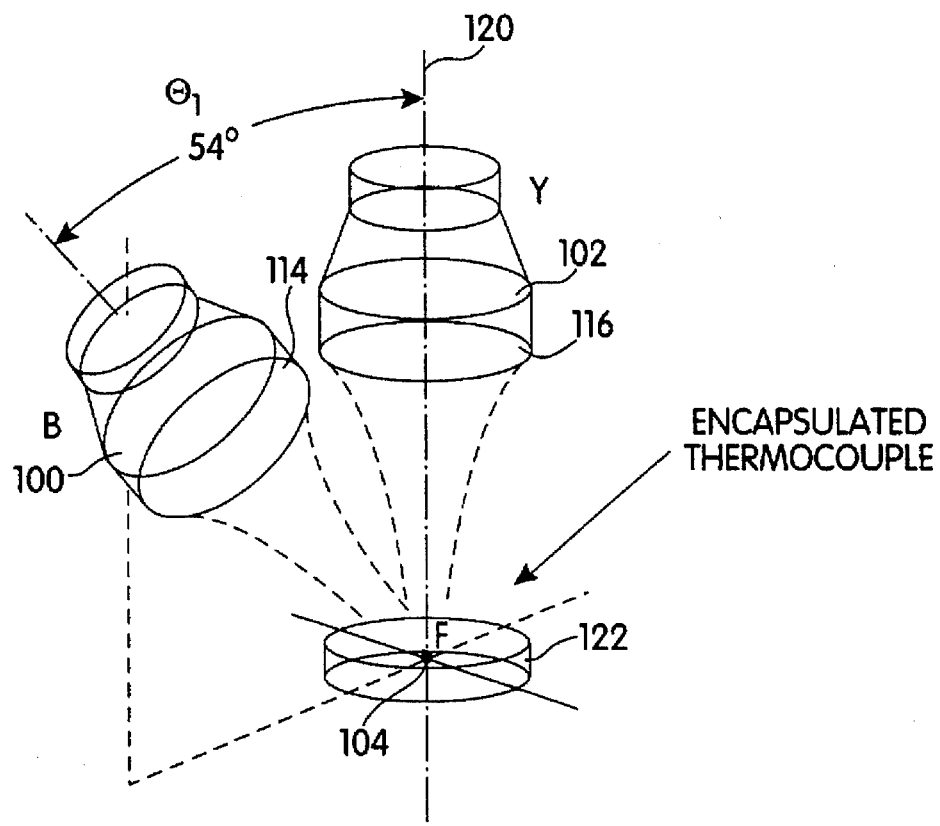
FIG. 4 illustrates an experimental arrangement of ultrasound transducers focused on an encapsulated thermocouple temperature probe for gathering hyperthermia data.
Figure 5:
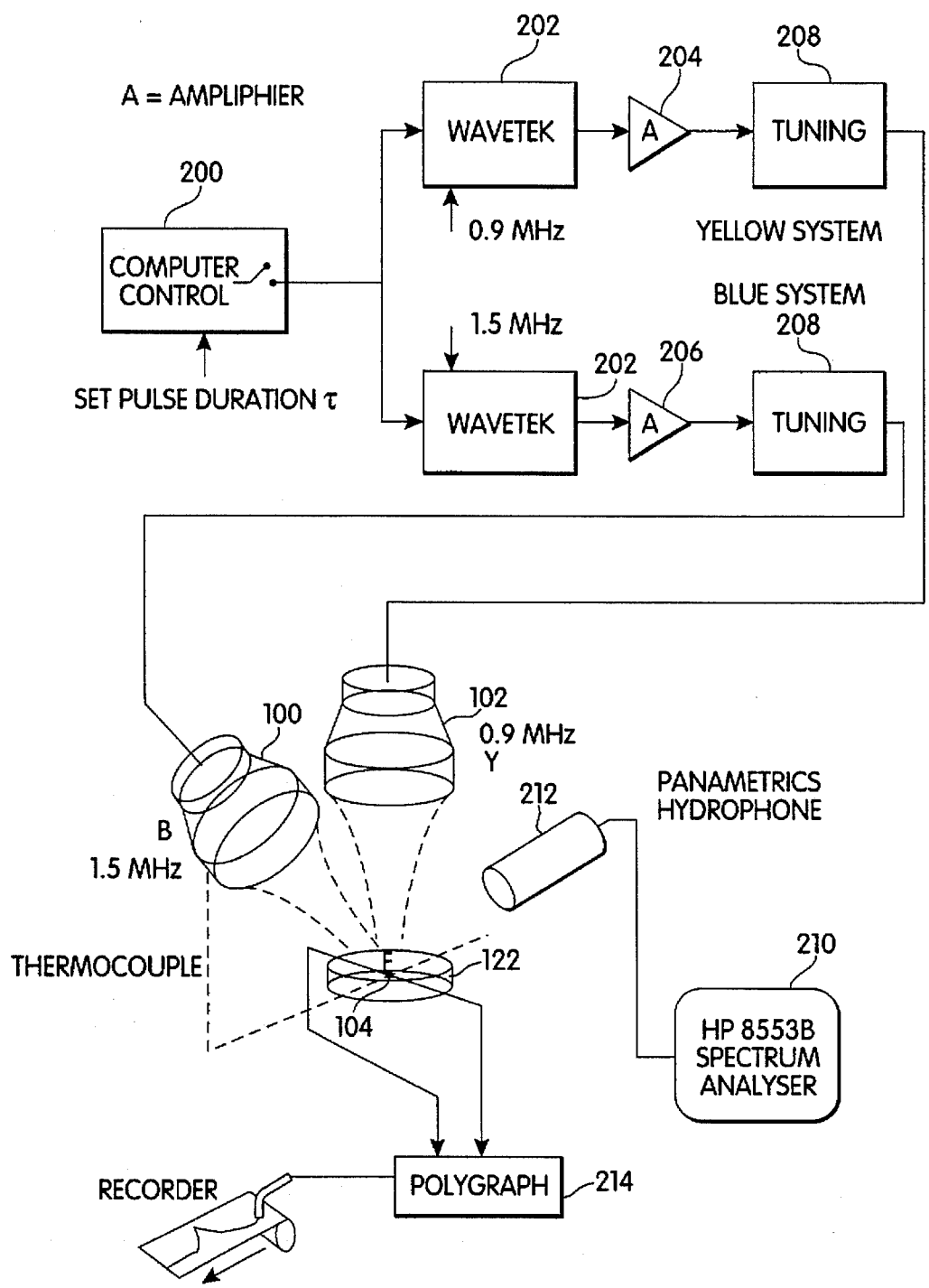
FIG. 5 is a schematic block diagram of an experimental apparatus for gathering hyperthermia data from the experimental arrangement of FIG. 4.

An experiment was conducted to verify the nonlinear enhanced heating mechanism of this invention. FIG. 4 shows the ultrasound transducer geometry used for the experiment and FIG. 5 shows a block diagram of the experimental instrumentation. The objective of this experiment was to determine if the heating within the confocal (intersecting) region F of two focused sound beams generated heat in a nonlinear way.

Two fixed-amplitude, fixed-focus ultrasound transducers 100 and 102, labeled B (Blue) and Y (Yellow) respectively, were arranged to have coincident foci F upon a silicone rubber 122 encapsulated thermocouple temperature probe 104. Ultrasound transducer B was pulsed for $\tau$ seconds at a frequency $f_B$=1.5 MHz and the temperature rise at the thermocouple probe was measured. Then, independently, ultrasound transducer Y was pulsed for $\tau$ seconds at a frequency $f_Y$=0.9 MHz and the temperature rise at the thermocouple probe was measured. The temperature changes for these two trials are denoted $\Delta T_B$ and $\Delta T_Y$ respectively. Finally, both ultrasound probes B and Y were simultaneously pulsed for $\tau$ seconds at their original frequencies and power levels, and the temperature rise at the thermocouple probe was measured, which is denoted as $\Delta T_{B+Y}$. A dimensionless ratio $\sigma_{heat}$ indicative of the nonlinear heat generation due to the intersection and interaction of the two ultrasound beams at F is defined to be $$\sigma_{heat} \equiv \frac{\Delta T_{B+Y}}{\Delta T_B + \Delta T_Y} \quad (1)$$

If the process of two sound beams interacting is a linear process, then the principle of superposition would hold and $\sigma_{heat}$ should equal 1.0. If the process is nonlinear, then $\sigma_{heat}$ should be >1.0, where the extra heat is due to sound energy transforming itself from the fundamental transmit frequencies for B and Y, into a spectrum of frequencies comprising the fundamental frequencies and mixing frequency products of those fundamental frequencies.

Ultrasound transducers 100 and 102 were quartz transducers with attendant transducer heads (not shown) water-sealing cones (flanges) (not shown) and lenses 114, 116, respectively. Each transducer head-cone combination contained degassed water sealed into each unit by means of stretched latex condom. Small air bubbles were removed from the sealed unit by the use of a syringe which was designed to attach to a special valve on the body of the water-seal cone. Thus, each transducer assembly was ensured of being free of any air bubbles for the duration of the experiment.

Each transducer head was mounted on a separate positioning mechanism (not shown). The 1.5 MHz Blue transducer was mounted on a six degree-of-freedom, motorized computer controlled platform (not shown), and was inclined to an angle $\theta_1$ of about 54° from the vertical axis 120. The 0.9 MHz Yellow transducer was mounted on a five degree-of-freedom, manually controlled platform (not shown), with the transducer aimed straight down along the vertical axis. Thus, the intermediate angle $\theta_1$ between the transducers was 54°. The position resolution of each platform was about 1 mm. Each transducer was calibrated for voltage versus radiation pressure (as measured in grams) using a Mettler PC 440 electronic scale. The power level chosen for each transducer was in the linear range based on the radiation pressure measurement.

The instrumentation used for the experiment, and shown in FIG. 5, included a computer 200 for controlling the B and Y transducer systems. Each transducer system included a Wavetek Model 278 waveform generator 202 independently controllable by the computer 200 to produce pulses of the desired duration at the desired frequency. The Y system waveform generator was set to 0.9 MHz and the B system waveform generator was set to 1.5 MHz. The output of each waveform generator 202 was connected to drive a power amplifier. In the case of the Yellow system, the output of waveform generator 202 drives power amplifier 204 which is an EIN RF power amplifier Model 3100L, which produces approximately 200W into a 50Ω load. In the case of the Blue system, the output of waveform generator 202 drives another amplifier 206 which was an IFI, Inc. (Farmingdale, N.Y.) Model M2600, which produces approximately 130 W into a 50Ω load. The output of each amplifier was coupled to its respective transducer through a tuning network 208.

The thermocouple probe 104 used for the experiment was constructed using a capacitive discharge butt weld technique to join together 0.003" (0.076 mm) diameter chromel and constantin Teflon-coated wires. The thermocouple bead at the junction of the two dissimilar wires was observed under a microscope and found to be free of oxide and not much larger than the wire diameter. A thermocouple capsule 122 was formed by encapsulating the thermocouple in General Electric RTV-615 silicone rubber using a 5.5 cm diameter, 0.75 cm deep petri dish mold. This encapsulant was chosen for its reasonable match to the ρc of water (i.e., ρ=1.02 g/cc), its transparency, and the relative ease with which the two encapsulant components are degassed after mixing, by means of a laboratory vacuum. The encapsulant also absorbs ultrasound to the same order of magnitude, per unit thickness, as certain types of human tissue. The DC resistance across the thermocouple leads was checked after welding, after encapsulation, and after the experiment to verify electrical continuity.

The encapsulated thermocouple (hereinafter referred to as the thermocouple) was mounted on a block of wedge-absorber polyethylene (not shown), which is similar to a glass fibre wedge absorber employed in air acoustic anechoic chambers. The polyethylene block was then placed at the bottom of an 8 gallon capacity acrylic-walled tank (not shown) filled with degassed water, and suitably weighted to prevent floatation and thermocouple movement. Several other polyethylene wedge absorbers were also randomly placed in the tank to enhance the absorption of echoes, and to reduce the quantity of degassed water needed to fill the tank.

The thermocouple was precalibrated using a cold reference ice bath. A Grass polygraph 210 (Model 7, Grass Instrument, Quincy, Mass.) was used to record the temperature of the thermocouple and was precalibrated for operation from 20° to 60° C. A small Panametrics transducer 212 ($f_r$=6 MHz) aimed at the confocal region was used to measure the ambient noise of the system during the tests by means of a Hewlett-Packard 8553B spectrum analyzer 214. This measurement was intended to identify finite amplitude harmonics, stable cavitation, and unstable cavitation.

With the thermocouple and transducers thus arranged and calibrated, a series of pulses were issued from each transducer to align each transducer focus with the thermocouple, starting with the Yellow 0.9 MHz system. When the two transducers were suitably arranged with foci believed to be coincident with the thermocouple, the experiment was ready to commence.

The protocol for the experiment was a test involving 10 pulses for B only, 10 pulses for Y only, and then 10 pulses for simultaneous B and Y transmission. The computer was programmed to give a 0.1 second duration pulse to simultaneously trigger the two waveform generators. The relatively long pulse duration, combined with the fast rise time of the electronics (capable of operation to at least 35 MHz) and the simultaneous triggering ensures overlap of the acoustic waves from the B and Y transducers as they travel through the confocal region, and gives adequate opportunity for nonlinear effects to occur.

Discussion and Conclusions

Figure 6:
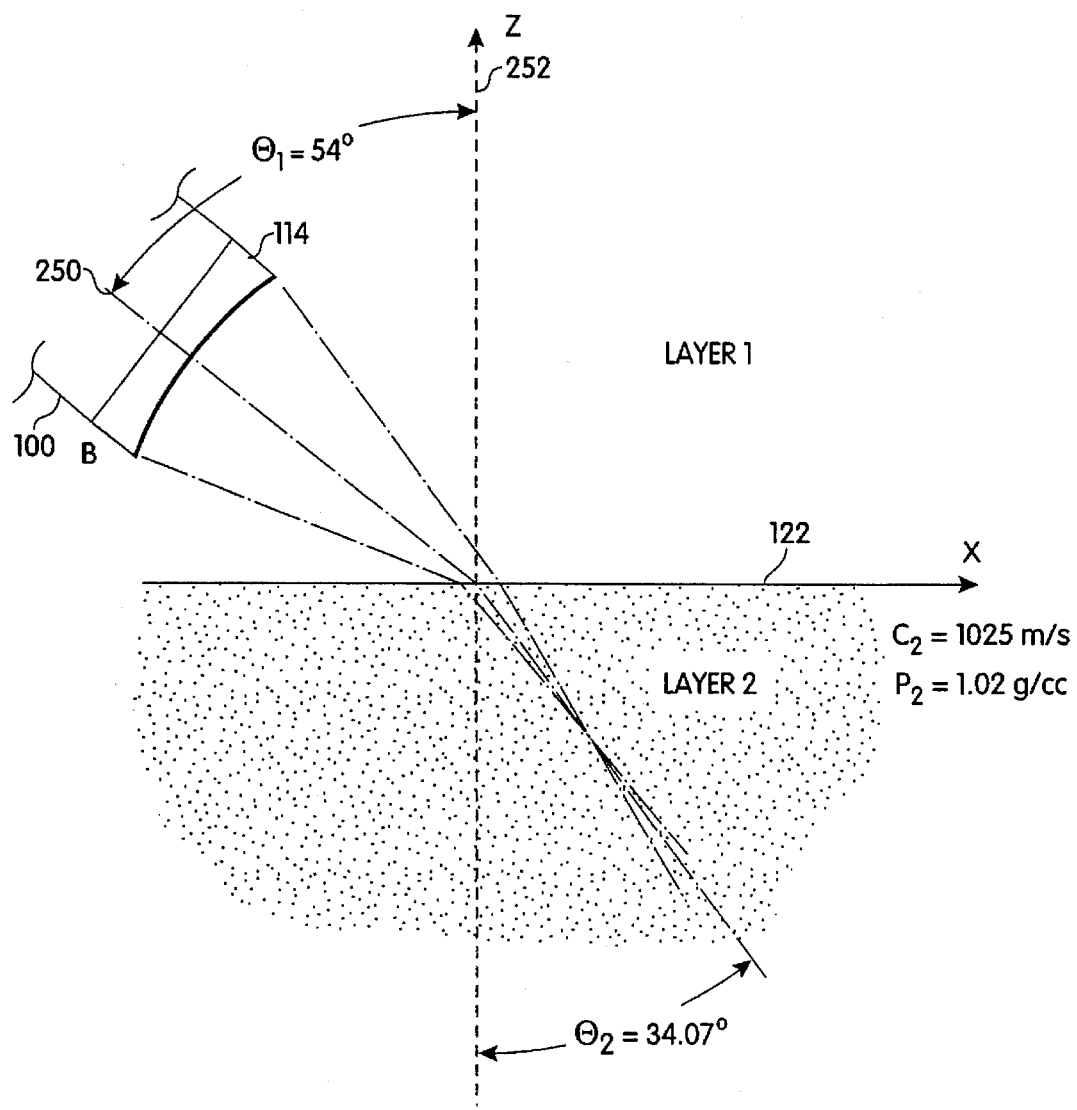
FIG. 6 is a section view of acoustic rays and refraction over the area surrounding the encapsulated thermocouple temperature probe of the experimental apparatus of FIG. 4.

FIG. 6 illustrates the geometry for the 1.5 MHz B transducer. The main radiation axis 250 is shown emanating from the lens 114 of the transducer into the water (layer 1) at an angle $\theta_1$=54° angle from the normal axis 252, and penetrating the silicone rubber (layer 2) at an angle $\theta_2$ from the normal axis. The speed of sound propagation in water is $c_1$=1480 m/sec, and in silicone rubber is $c_2$=1025 m/sec. Since $c_1 > c_2$, the waves will always propagate from the water and into the silicone rubber. We observe this by assuming that any wavelength in layer 1 projects a trace wavelength at the layer 1/layer 2 interface, and this trace wavelength must likewise match the projected wavelength in layer 2. This is merely Snell's law, and thus $$\text{projected trace wavelength} = \frac{\lambda_1}{\sin\Theta_1} = \frac{\lambda_2}{\sin\Theta_2} \qquad (2)$$

where, $$\lambda_n = \frac{c_n}{f} \qquad (3)$$

thus, $$\frac{c_1}{\sin\Theta_1} = \frac{c_2}{\sin\Theta_2} \qquad (4)$$

-continued
$$\frac{1480}{\sin 54°} = \frac{1025}{\sin \Theta_2}$$

$\Theta_2 = 34.07°$.

The inclination angle of a small streak of cavitation bubbles embedded in the rubber (about 1 cm from the thermocouple, and created during focal alignment but not during the actual measurements) was measured at 33.7° from the normal, thereby experimentally confirming this result.

Figure 7:
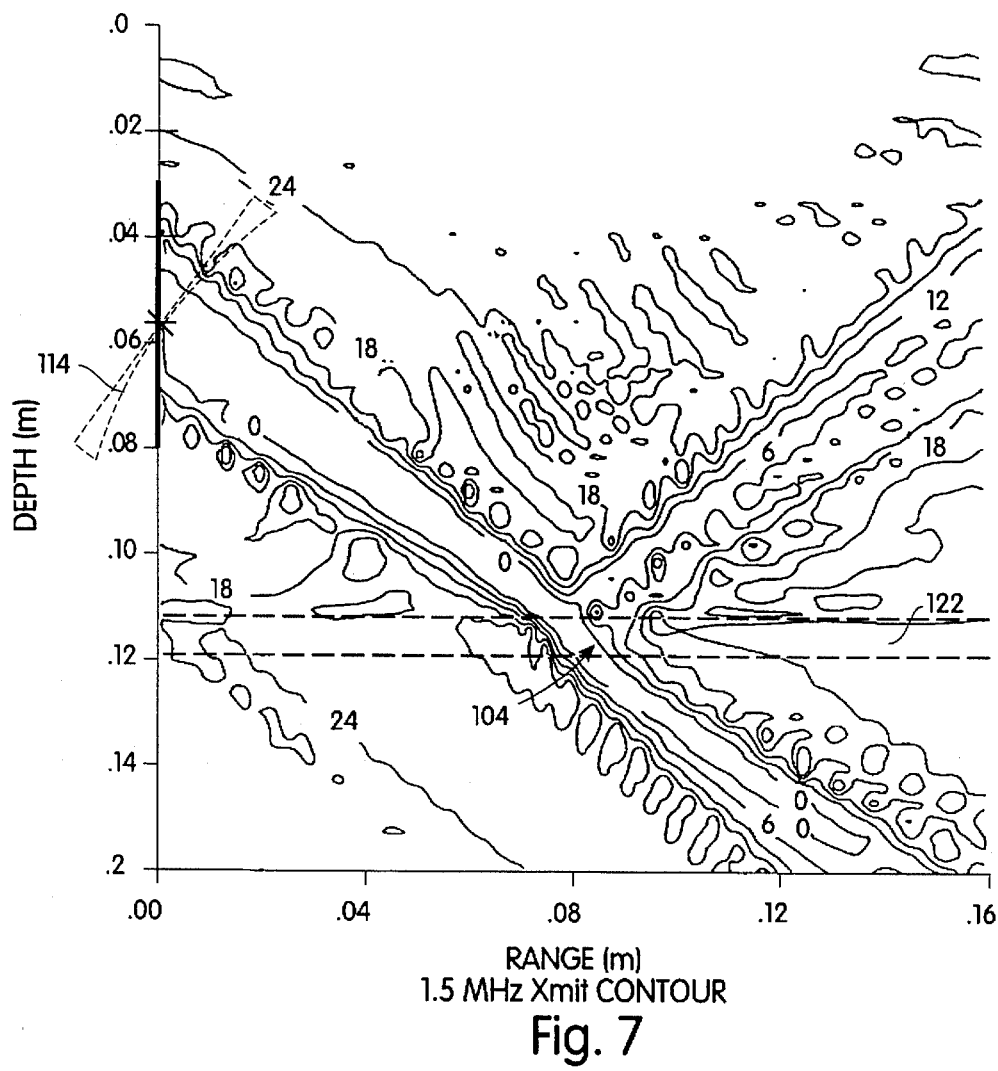
FIG. 7 is a computer model illustration of an acoustic wave being refracted by the thermocouple encapsulant of the experimental apparatus of FIG. 5.

The propagation of the oblique 1.5 MHz B transducer waves was modeled using the well known SAFARI computer code to produce a contour plot of transmission loss shown in FIG. 7. (see, Schmidt, H., "SAFARI: Seismo-Acoustic Fast Field Algorithm for Range Independent Environments. User's Guide.", SR 113, SACLANT ASW Research Centre, La Spezia, Italy (1987)). The focused 1.5 MHz B transducer was replaced in the model by a similarly focused line array 260 shown at the extreme left side of FIG. 7 at a depth of about 0.03 to 0.08 meters (note the dashed lines showing the focusing lens 114, and the dark solid line for the line array 260). The silicone rubber encapsulant 122 location is shown by the two parallel dashed lines at 0.1117 and 0.1187 meters depth. The air-water interface exists at zero depth, and the remaining regions above and below the silicone rubber are water. The thermocouple location 104 is shown by a small black triangle at depth=0.1115 meters, and range=0.0817 meters. Note that the thermocouple is not exactly at the focus center due to the refraction of the silicone rubber.

The SAFARI model creates full-wave solutions for two-dimensional linear acoustic wave propagation problems in layered media. In this case, the approximations made are that the circular-symmetry focused transducer is replaced by a similarly sized, 100-element focused line array 260 ($\lambda/2$ spacing), and the model is 2-D (range and depth). The contours represent the sound field transmission loss in 6 dB increments, and absorption is included for both sound waves in the water, and for longitudinal (sound) and shear waves in the silicone rubber. The input file for the model is included at the top of the figure.

Appendix A includes the data obtained from the thermocouple during performance of the experiment. Calculations summarizing the data are shown in Table I. These calculations show that the linear sum of the measured temperature increase at the thermocouple probe caused by the B and Y transducers operated at different times resulted in a total 12.7° C. temperature increase. In contrast, the measured temperature increase at the probe caused when the B and Y transducers were operated simultaneously was 13.5° C. Thus, simultaneous operation of the B and Y transducers resulted in a 0.8° C. greater temperature increase for the same electrical input power to the transducers. This corresponds to a $\sigma_{heat}$ at of 1.065, which indicates a 6.5% heat gain of the system due to the nonlinear interaction of the two focused ultrasound beams at the thermocouple probe.

The presence of ambient second harmonics during the B, Y, and B+Y tests strongly suggests the presence of nonlinear effects either from the acoustic drive levels themselves, or from nonlinear effects. The second harmonics could also be a consequence of stable cavitation, but this could not be confirmed due to the local oscillator spectral line of the analyzer interfering with the measurement of stable cavitation subharmonics. Third and fourth harmonics were not observed suggesting that the system could be driven harder, and there was no evidence of broadband impulsive noise suggesting that there was no unstable cavitation. Microscope inspection of the encapsulated thermocouple after all tests showed no evidence of cavitation bubbles anywhere along the thermocouple wire.

To assess cavitation, we can estimate the acoustical intensity in Watts/cm² at both the surface of the lens and at the focus for each of the B and Y transducers and compare them to established values for cavitation threshold in the literature. This is done by the following:

$$\text{lens projected area} = \frac{\pi}{4} (6.2)^2 = 30.19 \text{ cm}^2$$

B (1.5 MHz): 12.8 W (input power from calibration)
Y (0.9 MHz): 1.3 W (input power from calibration)
lens surface intensity: B: 12.8/30.2=0.42 W/cm² Y: 1.3/30.2=0.043 W/cm²

$$\text{focal diameter } d_f = 1.22 \frac{\lambda f}{a},$$

where
$\lambda$=wavelength, f=focal length (101 mm), a=lens radius (31 mm)
B (1.5 MHz): $d_f$=0.321 cm
Y (0.9 MHz): $d_f$=0.535 cm $$\text{focus section area } A_{focus} = \frac{\pi}{4} (d_f)^2, \text{cm}^2$$

B (1.5 MHz): $A_f$=0.0809 cm²
Y (O.9 MHz): $A_f$=0.2248 cm²
focal intensity: B: 12.8/0.0809=158 W/cm² Y: 1.3/0.2248=5.78 W/cm²

These estimates for focal intensity assume no absorption in either the water or in the silicone rubber. To account for absorption we multiply the absorption-free intensity by the following (for GE RTV-615, $\mu$=1.44 dB cm⁻¹ MHz⁻¹):

Y (0.9 MHz):
 $\mu_{0.9}$=1.296 dB/cm
 $\alpha_{0.9}=\mu_{0.9}/8.686$=0.149 Nepers/cm
 $\alpha_{0.9\text{-}power}=2\alpha_{0.9}$=0.298 Nepers/cm coefficient of transmission at normal
 incidence=0.95

$$\begin{aligned} I_{Y\text{-}focus} &= (5.78 \text{ W/cm}^2)(0.95) e^{-(.298 \times .35 cm)} \\ &= 5 \text{ W/cm}^2 \end{aligned}$$

B (1.5 MHz):
 $\mu_{1.5}$=2.16 dB/cm
 $\alpha_{1.5}=\mu_{1.5}/8.686$=0.249 Nepers/cm
 $\alpha_{1.5\text{-}power}=2'_{1.5}$=0.497 Nepers/cm coefficient of transmission at normal
 incidence=0.48

$$\begin{aligned} I_{B\text{-}focus} &= (158 \text{ W/cm}^2)(0.48) e^{-(.497 \times .7 cm)} \\ &= 54.3 \text{ W/cm}^2 \end{aligned}$$

These values suggest two things. First, the $\Delta T$ for the Y and B systems were both about 6° C. and yet the intensities at the focus were an order of magnitude different. This implies that the B system (1.5 MHz) did not have its true focus aligned with the thermocouple, but instead a focal sidelobe was present. This is reasonable because the two transducers could not have been moved any closer to each other with the lenses and the 54° separation angle used. Noting the focal displacement due to refraction in FIG. 7, it is entirely possible that the B system was not adequately aligned. Thus, the theoretical peak focal intensity is 54 W/cm² for the 1.5 MHz system, however the actual intensity at the thermocouple was reduced by an order of magnitude because the temperature increases were about the same. If we assume that the Y system was properly aligned with the thermocouple, then we may assume that the intensity for each of the systems was about 5 W/cm², and it is these intensities which are responsible for the heat generation.

The second feature is that the peak focal intensities in degassed water are well below the estimates for unstable cavitation, and below the levels considered for stable cavitation. Therefore, the extra heat supplied by two transducers firing simultaneously cannot be attributed to either cavitation phenomena.

From the thermocouple data listed in Appendix A, the thermoelectric voltage change for the temperature range from 20 to 26° C. (for a pulse from either the B or the Y system) is:

$$\begin{array}{cc} 26 & 1.556 \\ \underline{20} & \underline{1.192} \\ 6° C. & .364 \text{ mV} \end{array}$$

The thermoelectric voltage change for the temperature range 20° to 32° C. (for the simultaneous pulsing from both B and Y systems) is:

$$\begin{array}{cc} 32 & 1.924 \\ \underline{20} & \underline{1.192} \\ 13° C. & .732 \text{ mV} \end{array}$$

From these two we may estimate the dimensionless nonlinearity parameter $\sigma_{T/C}$ associated with the thermocouple by the same ratio used in finding $\sigma_{heat}$. That is $$\sigma_{T/C} = \frac{0.732}{(0.364 + 0.364)} = 1.0055. \tag{5}$$

Likewise from the data in Appendix A, we note that the amplitude linearity for the Grass polygraph oscilloscope is 2% full-scale. Since full-scale for this experiment was 40° C., then a 12° C. temperature rise represents, at worst, 30% of the full-scale error, or 0.6%. The dimensionless nonlinearity parameter for the oscilloscope recorder is then 1.006. We note that the parameters for both the thermocouple and for the oscilloscope recorder are below the $\sigma_{heat}$ parameter. Furthermore, the combined nonlinearity associated with the thermocouple and the recorder is the multiplication of the two, which gives 1.015. This is still too small to account for the $\sigma_{heat}=1.065$ from the experimental data.

One final comment is that the contamination of the heat transfer between the B, Y, and B+Y experiments. The thermocouple wire and the encapsulant together provide the heat conduction path for the thermocouple bead. During the solo trials for B, and for Y, the temperature rise was about 6° C. With both B and Y transmitting, the temperature rise was about 13° C. Since the temperature rise was about twice as high during the B+Y trials as it was during the solo B, or solo Y trials, the heat transfer rate would likewise be twice as fast. What this empirically suggests is that the heat conduction during the B+Y trials was more severe than in the B and Y trials, and so the B+Y trial was contaminated more than the B or the Y. The heat transfer mechanism reduces the maximum temperature that either the B+Y, the B, or the Y could reach, but it influences the B+Y about twice as much as the B, or the Y trials. This means that the heat transfer mechanism actually reduces the value of $\sigma_{heat}$. A heat transfer model could estimate the amount of the reduction, but for the purposes of this experiment, it is sufficient to note that the heat transfer comparison between the solo trials, and the simultaneous trials, is a source of experimental error that reduces $\sigma_{heat}$. This is in contrast to the errors associated with the thermocouple and the recorder.

The lack of unstable cavitation at the thermocouple site, the lack of sufficient nonlinearity in the thermocouple and in the polygraph, the acoustical intensities below the cavitation threshold, and $\sigma_{heat} > 1.0$ strongly support the existence of nonlinear heat generation from confocal ultrasound transducers.

While this invention has been particularly shown and described with references to preferred embodiments thereof, it will be understood by those skilled in the art that various changes in form and details may be made therein without department from the spirit and scope of the invention as defined by the appended claims. For instance, other means for generating ultrasound may be used, or the techniques described herein may be mixed, e.g., a single crystal transducer and a phased array transducer may be combined in the same hyperthermia apparatus. This invention may be implemented from a plurality of unfocused transducers, focused transducers, or electronically steered and/or focused arrays. A variety of waveforms may also be used to drive the plurality of sources. The sources may radiate the same waves, different waves, modulated waves, or radiate a combination of waves as a means to enhance the nonlinear interaction. Although this invention has been described with respect to ultrasound hyperthermia of biological tissue, there are other important areas which use ultrasound for heating which may benefit from this invention, for instance the materials processing industry. Furthermore, this invention applies to other types of waves which propagate in a medium in a nonlinear manner, or which may otherwise be made to interact in a nonlinear fashion. For example, the main discussions herein have referred to acoustic wave propagation, which is a longitudinal compression-rarefaction wave. There may be instances in material processing where the nonlinear interaction of transverse shear waves in solids may benefit from enhanced heating.

We claim:

1. An ultrasound hyperthermia applicator for heating a tissue mass target within a human body, comprising first ultrasound hyperthermia source means for producing ultrasound energy having a frequency $f_0$ between about 50 Khz and 5 Mhz;

first focusing means for focusing the energy from the first ultrasound hyperthermia source means and for producing a first focused ultrasound beam for heating the target;

second ultrasound hyperthermia source means for producing ultrasound energy having a frequency $f_1$ between about 50 Khz and 5 Mhz;

second focusing means for focusing the energy from the second ultrasound hyperthermia source means and for producing a second focused ultrasound beam for heating the target;

aiming means for directing the first and second focused ultrasound beams at the target to be heated so that the first and second ultrasound beams cross each other at the target, and the focus of the first and the second ultrasound beams are substantially coincident where the beams cross; and control means for activating the first and second ultrasound hyperthermia source means to provide simultaneous irradiation of the target by each of the first and second focused ultrasound beams to heat the target;

wherein the first and second ultrasound hyperthermia source means provide ultrasound energy sufficient for producing intermodulation products at the target where the first and second focused ultrasound beams cross, and wherein the intermodulation products including integral multiples of sum-frequencies $f_0+f_1$ which are absorbed by the target to provide additional heat to the target and the intermodulation products are absorbed by the tissue mass target at a substantially greater rate than ultrasound energy having a frequency of either $f_0$ or $f_1$ or a linear superposition of $f_0$ and $f_1$.

2. The apparatus of claim 1 wherein the first and second ultrasound hyperthermia source means produce ultrasound energies having substantially the same frequency.

3. The apparatus of claim 1 wherein the aiming means is adapted to direct the first and second beams at the tissue mass which is located within the cranium.

4. The apparatus of claim 1 wherein the first and second ultrasound hyperthermia source means produce ultrasound energies having substantially the same frequency.

5. The apparatus of claim 1 wherein the first ultrasound hyperthermia source means produces ultrasound energy which is a CW ultrasound signal having a frequency of $f_0$.

6. The apparatus of claim 1 wherein the first ultrasound hyperthermia source means produces ultrasound energy which is a bandlimited modulated signal having a center frequency of $f_0$.

7. The apparatus of claim 6 wherein the second ultrasound hyperthermia source means produces ultrasound energy which is a CW ultrasound signal having a frequency of $f_1$.

8. The apparatus of claim 6 wherein the second ultrasound hyperthermia source means produces ultrasound energy which is a bandlimited modulated ultrasound signal having a center frequency of $f_1$.

9. The apparatus of claim 1
wherein the first ultrasound hyperthermia source means comprises:
 a first signal generator means for producing a first gated ultrasound output signal at frequency $f_0$ in response to an input control signal generated by the control means; and
 a first power amplifier coupled to the output of the first signal generator means for amplifying the first gated ultrasound output signal;
the first focusing means comprises:
 a first ultrasound transducer coupled to the first power amplifier for converting the first amplified gated ultrasound output signal into the first focused ultrasound beam;
the second ultrasound hyperthermia source means comprises:
 a second signal generator means for producing a second gated ultrasound output signal at frequency $f_1$ in response to another input control signal generated by the control means;
 a second power amplifier coupled to the output of the second signal generator means for amplifying the second gated ultrasound output signal; and
the second focusing means comprises:
 a second ultrasound transducer coupled to the second power amplifier for converting the second amplifier gated ultrasound output signal into the second focused ultrasound beam.

10. The apparatus of claim 9, wherein each of the first and second ultrasound transducers comprises an acoustic lens for focusing its corresponding ultrasound beam at the target.

11. The apparatus of claim 10, wherein the aiming means comprises means for fixing the first and second ultrasound transducers relative to each other so that the first and second ultrasound beams cross each other at a predetermined angle, with coincident foci.

12. The apparatus of claim 9 wherein the first signal generator means produces the first gated ultrasound output signal which is a CW signal having a frequency of $f_0$.

13. The apparatus of claim 9 wherein the first signal generator means produces the first gated ultrasound output signal which is a bandlimited modulated signal having a center frequency $f_0$.

14. The apparatus of claim 13 wherein the second signal generator means produces the second gated ultrasound output signal which is a CW signal having a frequency $f_1$.

15. The apparatus of claim 13 wherein the second signal generator means produces the second gated ultrasound output signal which is a bandlimited modulated signal having a center frequency of $f_1$.

16. The apparatus of claim 1
wherein the first and second ultrasound hyperthermia source means produce ultrasound energies having substantially the same frequency,
wherein the first and second ultrasound hyperthermia source means comprise:
 a signal generator means for producing a gated ultrasound signal at frequency $f_0$ and $f_1$ in response to an input control signal generated by the control means;
 a power amplifier coupled to the output of the signal generator means for amplifying the gated ultrasound signal; and
 a power splitter coupled to the output of the amplifier for dividing the amplified gated ultrasound signal between a first power splitter output and a second power splitter output;
wherein the first focusing means comprises a first ultrasound transducer coupled to the first power splitter output for converting the amplified gated ultrasound signal into the first focused ultrasound beam; and
wherein the second focusing means comprises a second ultrasound transducer coupled to the second power splitter output for converting the amplified gated ultrasound signal into the second focused ultrasound beam.

17. The apparatus of claim 16, wherein each of the first and second ultrasound transducers comprises an acoustic lens for focusing its corresponding ultrasound beam at the target.

18. The apparatus of claim 16, wherein the aiming means comprises means for fixing the first and second ultrasound transducers relative to each other so that the first and second ultrasound beams cross each other at a predetermined angle with coincident foci.

19. The apparatus of claim 16 wherein the signal generator means produces the gated ultrasound signal which is a CW signal having a frequency $f_0$.

20. The apparatus of claim 16 wherein the signal generator means produces the gated ultrasound signal which is a bandlimited modulated signal having a center frequency $f_0$.

21. The apparatus of claim 1, wherein
the first ultrasound source means comprises a first phased array ultrasound transducer coupled to a first ultrasound scanner for generating a first steerable ultrasound beam at frequency $f_0$;
the second ultrasound source means comprises a second phased array ultrasound transducer coupled to a second ultrasound scanner for generating a second steerable ultrasound beam at frequency $f_1$; and
the aiming means further comprises means for electronically steering the first and second ultrasound beams.

22. The apparatus of claim 21, wherein each of the first and second ultrasound scanners comprises means for electronically focusing its corresponding ultrasound beam at the target.

23. The apparatus of claim 21, wherein the aiming means comprises means for fixing the first and second phased array ultrasound transducers relative to each other so that the first and second ultrasound beams can be electronically steered to cross each other at a predetermined angle with coincident foci.

24. The apparatus of claim 21 wherein the first ultrasound source means produces a CW ultrasound signal having a frequency of $f_0$.

25. The apparatus of claim 21 wherein the first ultrasound source means produces a bandlimited modulated signal having a center frequency of $f_0$.

26. The apparatus of claim 25 wherein the second ultrasound source means produces a CW ultrasound signal having a frequency of $f_1$.

27. The apparatus of claim 25 wherein the second ultrasound source produces a bandlimited modulated ultrasound signal having a center frequency of $f_1$.

28. A method for heating a target with ultrasound, comprising the steps of
producing a first focused ultrasound beam having a frequency $f_0$ between about 50 kHz and 5 MHz with a first ultrasound hyperthermia source;
producing a second focused ultrasound beam having a frequency $f_1$ between about 50 kHz and 5 MHz with a second ultrasound hyperthermia source;
directing the first and second focused ultrasound beams at the target to be heated so that the first and second ultrasound beams cross each other at the target, and the focus of the first and second ultrasound beams are substantially coincident where the beams cross; wherein
the first and second ultrasonic beams have sufficient ultrasound energy to produce intermodulation products at the target where the first and second ultrasound beams cross, and wherein the intermodulation products include integral multiples of sum-frequencies $f_0+f_1$ which are absorbed by the target to provide additional heat to the target and the intermodulation products are highly absorbed by the target at a substantially greater rate than ultrasound energy having a frequency of either $f_0$ or $f_1$ or a linear superposition of $f_0$ and $f_1$.

29. The method of claim 28, wherein frequency $f_0$ is substantially the same as frequency $f_1$.

30. The method of claim 28 wherein the directing step further comprises directing the ultrasound beams at a tissue mass located within a human cranium.

31. The method of claim 28, further comprising the step of fixing the first and second ultrasound sources relative to each other so that the first and second ultrasound beams cross each other at a predetermined angle with coincident foci.

32. The method of claim 28 wherein the first ultrasound source produces a CW ultrasound signal having a frequency of $f_0$.

33. The method of claim 28 wherein the first ultrasound source produces a bandlimited modulated signal having a center frequency of $f_0$.

34. The method of claim 33 wherein the second ultrasound source produces a CW ultrasound signal having a frequency of $f_1$.

35. The method of claim 33 wherein the second ultrasound source produces a bandlimited modulated ultrasound signal having a center frequency of $f_1$.

36. The method of claim 28, wherein
producing the first ultrasound beam comprises providing a first phased array ultrasound transducer coupled to a first ultrasound scanner for generating a first steerable ultrasound beam at frequency $f_0$;
producing the second ultrasound beam comprises providing a second phased array ultrasound transducer coupled to a second ultrasound scanner for generating a second steerable ultrasound beam at frequency $f_1$; and
directing the first and second ultrasound beams comprises electronically steering the first and second ultrasound beams.

37. The method of claim 36, further comprising the step of electronically focusing the first and second ultrasound beams at the target.

38. The apparatus of claim 36, wherein the directing step further comprises the steps of
fixing the first and second phased array ultrasound transducers relative to each other, and
electronically steering the first and second beams to cross each other at a predetermined angle with coincident foci.

39. An ultrasound hyperthermia applicator for heating a target, comprising
a plurality of N ultrasound hyperthermia source means which each produces an ultrasound energy having a corresponding frequency $f_n$ between about 50 kHz and 5 MHz, where n is from 1 to N;
a plurality of focusing means which each focuses the energy from a different one of the hyperthermia source means and produces one of N focused ultrasound beams for heating the target;
aiming means for directing the N focused ultrasound beams at the target to be heated so that the N ultrasound beams cross each other at the target, and the focus of each of the N ultrasound beams are substantially coincident where the beams cross; and
control means for activating the N ultrasound hyperthermia source means to provide simultaneous irradiation of the target by each of the N focused ultrasound beams to heat the target;
wherein the N ultrasound hyperthermia source means provide sufficient ultrasound energy for producing intermodulation products at the target where the N ultrasound beams cross, and wherein the intermodulation products include integral multiples of sum frequencies of the corresponding frequencies $f_n$ which are absorbed by the target to provide additional heat to the target and the intermodulation products are highly absorbed by the target at a substantially ultrasound energy having a frequency of of $f_n$ or a linear superposition of $f_n$.

40. The apparatus of claim 39 wherein the plurality of N ultrasound hyperthermia source means produce ultrasound energies having substantially the same frequency.

41. An ultrasound hyperthermia applicator for heating a target, comprising
first ultrasound hyperthermia source means for producing ultrasound energy having a frequency $f_0$ between about 50 Khz and 5 Mhz;
first focusing means for focusing the energy from the first ultrasound hyperthermia source means and for producing a first focused ultrasound beam for heating the target;
second ultrasound hyperthermia source means for producing ultrasound energy having a frequency $f_1$ between about 50 Khz and 5 Mhz;

second focusing means for focusing the energy from the second ultrasound hyperthermia source means and for producing a second focused ultrasound beam for heating the target;

aiming means for directing the first and second focused ultrasound beams at the target to be heated so that the first and second ultrasound beams cross each other at a plurality of selectable points within a three-dimensional region which includes the target, and the focus of the first and the second ultrasound beams are substantially coincident at the plurality of selectable points where the beams cross; and control means for activating the first and second ultrasound hyperthermia source means to provide simultaneous irradiation of the target by each of the first and second focused ultrasound beams to heat the target at the plurality of selectable points;

wherein the first and second ultrasound hyperthermia source means provide sufficient ultrasound energy for producing intermodulation products at the plurality of selectable points where the first and second focused ultrasound beams cross, and wherein the intermodulation products include integral multiples of sum-frequencies $f_0+f_1$ which are absorbed by the target at the plurality of selectable points to provide additional heat to the target and the intermodulation products are highly absorbed by the target at a substantially greater rate than ultrasound energy having a frequency of either $f_0$ or $f_1$ or a linear superposition of $f_0$ and $f_1$.

42. An ultrasound hyperthermia applicator for heating a target, comprising first ultrasound hyperthermia source means for producing ultrasound energy which is a triangular wave broadband signal rich in harmonics of a fundamental frequency $f_0$ between about 50 Khz and 5 Mhz;

first focusing means for focusing the energy from the first ultrasound hyperthermia source means and for producing a first focused ultrasound beam for heating the target;

second ultrasound hyperthermia source means for producing ultrasound energy which is a triangular wave broadband signal rich in harmonics of a fundamental frequency $f_1$;

second focusing means for focusing the energy from the second ultrasound hyperthermia source means and for producing a second focused ultrasound beam for heating the target;

aiming means for directing the first and second focused ultrasound beams at the target to be heated so that the first and second ultrasound beams cross each other at the target, and the focus of the first and the second ultrasound beams are substantially coincident where the beams cross; and control means for activating the first and second ultrasound hyperthermia source means to provide simultaneous irradiation of the target by each of the first and second focused ultrasound beams to heat the target;

wherein the first and second ultrasound hyperthermia source means and provide broadband signals which are rich in harmonics for producing a similarly rich variety of intermodulation products at the target where the first and second focused ultrasound beams cross, and wherein the intermodulation products include integral multiples of sum-frequencies $f_0+f_1$ which are easily absorbed by the target to provide additional heat to the target and the intermodulation products are highly absorbed by the target at a substantially greater rate than ultrasound energy having a frequency of either $f_0$ or $f_1$ or a linear superposition of $f_0$ and $f_1$.

43. An ultrasound hyperthermia applicator for heating a target, comprising first ultrasound hyperthermia source means for producing ultrasound energy having a frequency $f_0$ between about 50 Khz and 5 Mhz;

first focusing means for focusing the energy from the first ultrasound hyperthermia source means and for producing a first focused main ultrasound beam for heating the target; second ultrasound hyperthermia source means for producing ultrasound energy having a frequency $f_1$ between about 50 Khz and 5 Mhz;

second focusing means for focusing the energy from the second ultrasound hyperthermia source means and for producing a second focused main ultrasound beam for heating the target;

aiming means for directing the first and second focused main ultrasound beams at the target to be heated so that the first and second main ultrasound beams cross each other at the target, and the focus of the first and the second main ultrasound beams are substantially coincident where the main beams cross; and control means for activating the first and second ultrasound hyperthermia source means to provide simultaneous irradiation of the target by each of the first and second focused main ultrasound beams to heat the target;

wherein the first and second ultrasound hyperthermia source means provide ultrasound energy sufficient for producing intermodulation products at the target where the first and second focused main ultrasound beams cross, and wherein the intermodulation products include integral multiples of sum-frequencies $f_0+f_1$ which are absorbed by the target to provide additional heat to the target and the intermodulation products are highly absorbed by the target at a substantially greater rate than ultrasound energy having a frequency of either $f_0$ or $f_1$ or a linear superposition of $f_0$ and $f_1$.

44. An ultrasound hyperthermia applicator for heating a target, comprising first ultrasound hyperthermia source means for producing ultrasound energy which is a modulated signal centered about a frequency $f_0$ between about 50 Khz and 5 Mhz, wherein the modulation is in the form of amplitude modulation, frequency modulation, or pseudo-random modulation;

first focusing means for focusing the energy from the first ultrasound hyperthermia source means and for producing a first focused ultrasound beam for heating the target;

second ultrasound hyperthermia source means for producing ultrasound energy which is a modulated signal centered about a frequency $f_1$ between about 50 Khz and 5 Mhz, wherein the modulation is in the form of amplitude modulation, frequency modulation, or pseudo-random modulation;

second focusing means for focusing the energy from the second ultrasound hyperthermia source means and for producing a second focused ultrasound beam for heating the target;

aiming means for directing the first and second focused ultrasound beams at the target to be heated so that the first and second ultrasound beams cross each other at the target, and the focus of the first and the second ultrasound beams are substantially coincident where the beams cross; and control means for activating the first and second ultrasound hyperthermia source means to provide simultaneous irradiation of the target by each of the first and second focused ultrasound beams to heat the target;

wherein the first and second ultrasound hyperthermia source means provide and ultrasound energy sufficient for producing intermodulation products at the target where the first and second focused ultrasound beams cross, and wherein the intermodulation products include integral multiples of sum-frequencies $f_0+f_1$ which are absorbed by the target to provide additional heat to the target and the intermodulation products are highly absorbed by the target at a substantially greater rate than ultrasound energy having a frequency of either $f_0$ or $f_1$ or a linear superposition of $f_0$ and $f_1$.

* * * * *